United States Patent [19]

Brunelle

[11] Patent Number: 5,321,117
[45] Date of Patent: Jun. 14, 1994

[54] MACROCYCLIC POLYESTER OLIGOMER PREPARATION WITH LEWIS ACID AS CATALYST

[75] Inventor: Daniel J. Brunelle, Scotia, N.Y.

[73] Assignee: General Electric Company, Schenectady, N.Y.

[21] Appl. No.: 978,583

[22] Filed: Nov. 19, 1992

[51] Int. Cl.$^5$ .................................. C08G 63/02
[52] U.S. Cl. ...................... 528/272; 528/274; 528/280; 528/281; 528/283; 528/285; 528/302; 528/308; 528/308.6; 525/437; 525/444; 524/81; 524/432; 524/435
[58] Field of Search ............... 528/272, 274, 280, 281, 528/283, 285, 302, 308, 308.6; 525/437, 444; 524/81, 432, 435

[56] References Cited

PUBLICATIONS

CA116(22):2154325; CA106(26):2144860; CA96(14):105110w CA89(14):110452u.
Droscher et al., "Poly(ethylene terephthalate): a solid Condensation Process", *Polymer*, vol. 19, 1978, pp. 43–47.
Goodman et al., "The Structures and Reversible Polymerization of Cyclic Oligomers from Poly(ethylene terephthalate)", *Polymer* 1, Sep. 1960, pp. 384–386.
Ross et al., "Isolation of a Cyclic Trimer from Polyethylene Terephthalate Film", *J. Polymer Sci.*, 3, 406–407 (1954).
Org. Syn., Coll. vol. 3, 141–142 (1955).

*Primary Examiner*—John Kight, III
*Assistant Examiner*—Sam A. Acquah
*Attorney, Agent, or Firm*—Edward A. Squillante; William H. Pittman

[57] ABSTRACT

Macrocyclic poly(alkylene dicarboxylate) oligomers are prepared by the reaction of a dicarboxylic acid chloride such as terephthaloyl chloride with at least one bis(hydroxyalkyl) ester such as bis(4-hydroxybutyl) terephthalate, in the presence of a Lewis acid as catalyst. Illustrative Lewis acids are ferric chloride, zinc chloride, zinc bromide, stannous bromide and antimony pentachloride.

14 Claims, No Drawings

MACROCYCLIC POLYESTER OLIGOMER PREPARATION WITH LEWIS ACID AS CATALYST

This invention relates to the preparation of macrocyclic polyester oligomer compositions, and more particularly to their preparation by a method employing a Lewis acid as catalyst.

Linear polyesters such as poly(ethylene terephthalate) and poly(butylene terephthalate) are well known commercially available polymers having advantageous properties including solvent resistance. They are normally prepared by the reaction of a diol with a functional derivative of a dicarboxylic acid, typically a diacid halide or ester.

Recently, methods have been developed for the preparation of macrocyclic poly(alkylene dicarboxylate) oligomer compositions (hereinafter sometimes simply "macrocyclic oligomers"). These compositions are noted for their low viscosity and consequent ease of handling. They are easily converted to linear polyesters by contact with various catalytic materials.

One method for macrocyclic oligomer preparation, disclosed in U.S. Pat. No. 5,039,783, involves the reaction of a diol with a dicarboxylic acid chloride (hereinafter sometimes "diacid chloride") under substantially anhydrous conditions and in the presence of a substantially water-immiscible organic solvent such as methylene chloride and at least one unhindered tertiary amine. Examples of suitable tertiary amines are quinuclidine and 1,4-diazabicyclo[2.2.2]octane (hereinafter "DABCO"). It is necessary to use the unhindered amine in large quantities, typically at least one mole and preferably more than one mole per mole of diol and diacid chloride combined. The reaction temperature is critical and is limited to the range from −25° to +25° C. At higher temperatures a proliferation of side reactions occurs, including reaction of the unhindered amine with methylene chloride or similar compounds employed as solvents and decomposition of the acylammonium salt formed by the reaction of the amine with the diacid chloride.

A variation of this method is described in copending, commonly owned application Ser. No. 07/709,256. It uses only a catalytic amount of the unhindered amine, with the remainder thereof being replaced by an acid-accepting amount of at least one other tertiary amine selected from the group consisting of trialkylamines and heteroaromatic tertiary amines. This method is advantageous in that the other amines are less expensive than the unhindered amines and reaction temperatures are not as critical, temperatures from −5° to about 40° C. typically being employed. However, a further disadvantage of both of these methods is the necessity to employ expensive dicarboxylic acid chlorides in large amounts.

The employment of bis(hydroxyalkyl dicarboxylates) (hereinafter sometimes "bis-esters") in the synthesis of individual macrocyclic oligomers is disclosed and claimed in copending, commonly owned application Ser. No. 07/964,996. This method requires the use of at least one unhindered tertiary amine as a catalyst and acid acceptor, or the use of such a compound as catalyst in combination with at least one other tertiary amine selected from the group consisting of trialkylamines and heteroaromatic tertiary amines as an acid acceptor. The unhindered amines are expensive, and any amine can cause the aforementioned side reactions. Moreover, the use of amines in acid-accepting proportions requires such burdensome operations as washing with acid for amine removal.

The present invention provides an alternative method for preparing macrocyclic polyester oligomers from bis(hydroxyalkyl dicarboxylates). Said method is frequently more convenient and inexpensive than the one which employs amines, since it is not as likely to cause side reactions and no step of amine removal from the product is necessary. It is possible merely to mix the two reagents in solution in the presence of a catalyst, whereupon the reaction proceeds smoothly. The catalyst employed is at least one Lewis acid.

Accordingly, the invention is a method for preparing a cyclic poly(alkylene dicarboxylate) oligomer composition which comprises contacting at least one dicarboxylic acid chloride of the formula

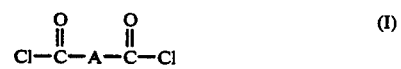

with an approximately equimolar amount of at least one bis(hydroxyalkyl) ester of the formula

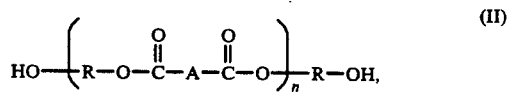

wherein each A is independently a m- or p-linked divalent monocyclic aromatic or alicyclic radical, R is an alkylene or mono- or polyoxyalkylene radical containing a straight chain of about 2–8 atoms and n is from 1 to about 5, in solution in at least one substantially water-immiscible solvent and in the presence of a catalytic amount of at least one Lewis acid selected from the group consisting of ferric chloride, zinc chloride, zinc bromide, stannous bromide and antimony pentachloride.

The A values in formulas I and II may be the same or different m- or p-linked monocyclic aromatic or alicyclic radicals. Included are m- and p-phenylene, substituted derivatives thereof, and similarly structured cyclohexylene and cyclopentylene radicals. The m- and p-phenylene radicals, and especially p-phenylene, are preferred.

The R value may be considered as being derived from a corresponding alkylene glycol or polyalkylene glycol, in which the straight chain connecting the hydroxy groups contains about 2–8 atoms. Suitable alkylene glycols include ethylene glycol, propylene glycol, tetramethylene glycol, hexamethylene glycol and neopentylene glycol. Suitable polyalkylene glycols include diethylene glycol and triethylene glycol. Ethylene glycol and tetramethylene glycol are preferred.

In the bis-esters of formula II, n may be from 1 to about 5 (including fractional values, signifying a mixture of oligomeric esters). It is preferably in the range of 1–3 and especially 1. For brevity, the bis-ester in which n is 1 is sometimes designated hereinafter "monomer diol". Mixtures of compounds with various n values may be employed. As previously mentioned, such bis-esters may be prepared by the conventional reaction of a dialkyl dicarboxylate such as dimethyl terephthalate, or a similar dialkyl ester of a linear poly(alkylene dicarboxylate) oligomer, with a diol of the formula HO—R—OH.

The crux of the invention is the reaction between a diacid chloride of formula I and a bis-ester represented by formula II. As organic solvents in said reaction, various water-immiscible organic liquids may be employed. Illustrative liquids of this type are aromatic hydrocarbons such as toluene and xylene; substituted aromatic hydrocarbons such as chlorobenzene, o-dichlorobenzene and nitrobenzene; and chlorinated aliphatic hydrocarbons such as chloroform, methylene chloride, trichloroethane and tetrachloroethane. Mixtures of solvents may also be employed. Chlorinated aliphatic and aromatic hydrocarbons are often preferred, with methylene chloride and chlorobenzene frequently being most preferred because of their availability and particular suitability.

In the method described in the aforementioned U.S. Pat. No. 5,039,783 and application Ser. No. 07/709,256, it was frequently advantageous to employ, in combination with solvents of the type disclosed above, a more polar combined oxygen-containing solvent such as tetrahydrofuran. The purpose of the more polar solvent was to facilitate dissolution of the diol reagent. Since a diol is not employed in the present invention, the employment of such a solvent is not necessary.

The catalysts whose use in the method of this invention is contemplated are Lewis acids. While the use of any Lewis acid may be appropriate, metal halides are especially appropriate and those specifically contemplated in accordance with the present invention are ferric chloride, zinc chloride, zinc bromide, stannous bromide and antimony pentachloride. The use of such Lewis acids as catalysts makes it unnecessary to employ the amines disclosed in the aforementioned application Ser. No. 07/964,996.

The reaction may be conducted by merely mixing the reagents and catalyst under relatively high dilution conditions. It is also feasible to employ "pseudo-high dilution" conditions; that is, to add solutions of the two reagents simultaneously to solvent and catalyst in a reaction vessel. The concentration of each of the reagents in solution in the reaction mixture is generally maintained in the range of about 0.01–0.05M.

The diacid chloride and bis-ester are employed in approximately equimolar amounts. Some variation, generally no more than about 5%, is permissible. The Lewis acid is generally present in the amount of about 0.1–2.0 mole percent, based on bis-ester. Reaction temperatures are typically in the range of about 30°–75° C.

Following the reaction between the diacid chloride and bis-ester, it may be necessary to remove linear polyester in the form of oligomers and high polymer. The high polymer portion of the linears is insoluble in the solvents employed, and may be removed by filtration. Linear oligomers may be removed by column chromatography through silica gel or the like. After any high polymer and linear oligomers have been removed, the solvent may be removed by distillation or evaporation and the cyclic oligomers recovered in substantially pure form.

The method of this invention is illustrated by the following examples. All percentages are by weight.

EXAMPLE 1

Terephthaloyl chloride, 20 mmol., in the form of a 1M solution in chlorobenzene, and 6.208 grams (20 mmol.) of bis(4-hydroxybutyl) terephthalate were mixed and the mixture was diluted to 0.02M by the addition of chlorobenzene. The solution was heated to reflux and 16 mg. (0.1 mmol.) of anhydrous ferric chloride was added, causing a modest gas evolution. The mixture was refluxed for 30 minutes, cooled to about 50° C. and diluted with an equal volume of methylene chloride. After filtration through a filter aid material, the solvent was evaporated on a rotary evaporator and the residue was dissolved in methylene chloride and passed through silica gel to remove linear oligomers. Evaporation of the methylene chloride yielded the desired macrocyclic poly(butylene terephthalate) oligomers in a total yield of 348 mg. (40% of theoretical). Analysis by high pressure liquid chromatography showed the presence of about 80% cyclic dimer, with smaller amounts of tetramer and hexamer.

EXAMPLE 2

A mixture of 10 ml. of a 1M solution in chlorobenzene of terephthaloyl chloride and 3.104 grams (10 mmol.) of bis(4-hydroxybutyl) terephthalate was dissolved in 10 ml. of methylene chloride and the solution was added via a syringe to a refluxing mixture of 80 mg. (0.5 mmol.) of anhydrous ferric chloride and 40 ml. of chlorobenzene. The gas which evolved during the reaction, as well as the methylene chloride, were swept from the flask by a stream of nitrogen. After addition was complete, the mixture was heated under reflux for 10 minutes, cooled to about 50° C., diluted with an equal volume of methylene chloride and filtered through a filter aid material. The filtrate was washed with water, dried, filtered and evaporated to yield 2.112 grams (48% of theoretical) of macrocyclic poly(butylene terephthalate) oligomers having a product distribution similar to that described in Example 1.

EXAMPLE 3

The procedure of Example 2 was repeated, replacing the ferric chloride on an equimolar basis with zinc bromide. The yield of macrocyclic oligomers was 36% of theoretical.

What is claimed is:

1. A method for preparing a cyclic poly(alkylene dicarboxylate) oligomer composition which comprises contacting at least one dicarboxylic acid chloride of the formula

with an approximately equimolar amount of at least one bis(hydroxyalkyl) ester of the formula

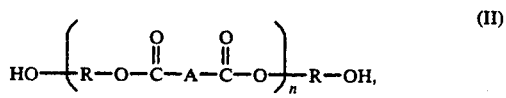

wherein each A is independently a m- or p-linked divalent monocyclic aromatic or alicyclic radical, R is an alkylene or mono- or polyoxyalkylene radical containing a straight chain of about 2–8 carbon atoms and n is from 1 to about 5, in solution in at least one substantially water-immiscible solvent and in the presence of a catalytic amount of at least one Lewis acid selected from the group consisting of ferric chloride, zinc chloride, zinc bromide, stannous bromide and antimony pentachloride.

2. A method according to claim 1 wherein R is alkylene.

3. A method according to claim 2 wherein R is ethylene or 1,4-butylene.

4. A method according to claim 3 wherein each A is independently m- or p-phenylene.

5. A method according to claim 2 wherein n is 1.

6. A method according to claim 2 wherein the Lewis acid is ferric chloride.

7. A method according to claim 2 wherein the Lewis acid is zinc chloride.

8. A method according to claim 2 wherein the Lewis acid is zinc bromide.

9. A method according to claim 2 wherein the Lewis acid is stannous bromide.

10. A method according to claim 2 wherein the Lewis acid is antimony pentachloride.

11. A method according to claim 2 wherein the reaction temperature is in the range of about 30°–75° C.

12. A method according to claim 2 wherein the solvent is a chlorinated aliphatic or aromatic hydrocarbon or a mixture thereof.

13. A method according to claim 12 wherein the solvent is chlorobenzene.

14. A method according to claim 2 wherein the concentration of each of the dicarboxylic acid chloride and bis(hydroxyalkyl) ester in solution in the reaction mixture is maintained in the range of about 0.01–0.05M.

* * * * *